Figure 1:
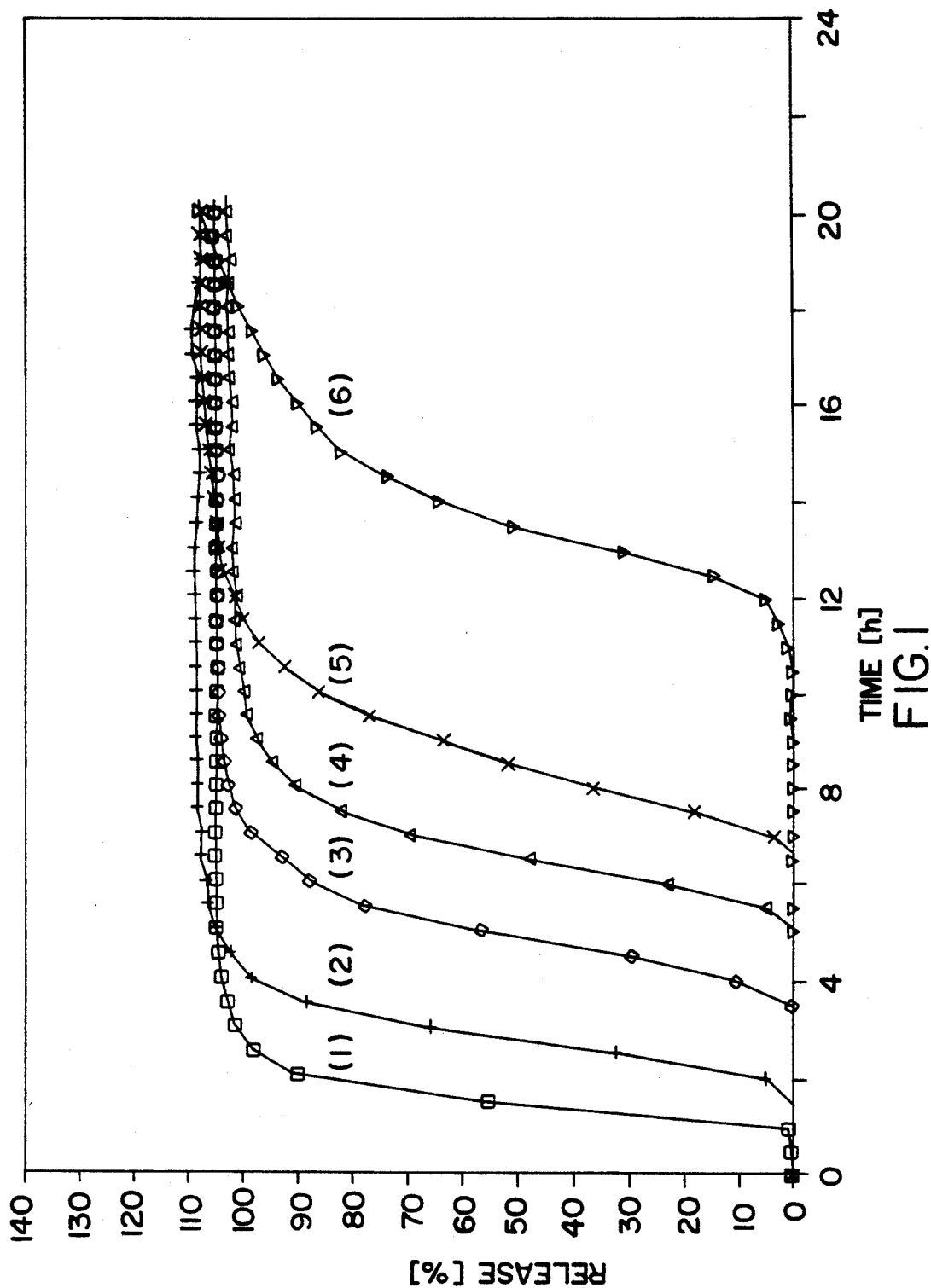

United States Patent [19]

Bücheler et al.

[11] Patent Number: 5,204,121
[45] Date of Patent: Apr. 20, 1993

[54] MEDICAMENTS HAVING CONTROLLED RELEASE OF THE ACTIVE COMPOUND

[75] Inventors: Manfred Bücheler, Overath; Andreas Ohm, Neuss; Roland Rupp, Leichlingen; Josef Schmoll, Wermelskirchen; Axel Wollenschläger, Leverkusen, all of Fed. Rep. of Germany

[73] Assignee: Bayer Aktiengesellschaft, Leverkusen, Fed. Rep. of Germany

[21] Appl. No.: 472,681

[22] Filed: Jan. 30, 1990

[30] Foreign Application Priority Data

Feb. 11, 1989 [DE] Fed. Rep. of Germany ....... 3904093

[51] Int. Cl.[5] .................. A61K 9/14; A61K 9/58; A61K 9/62
[52] U.S. Cl. .................. 424/495; 424/494; 424/497; 424/498; 424/461; 424/462
[58] Field of Search .............. 424/489, 490, 497, 501, 424/495, 494, 462, 461, 498

[56] References Cited

U.S. PATENT DOCUMENTS

| 4,533,562 | 8/1985 | Ikegami et al. | 427/3 |
|---|---|---|---|
| 4,800,087 | 1/1987 | Mehta | 424/497 |
| 4,994,279 | 2/1991 | Aoki et al. | 424/494 |

FOREIGN PATENT DOCUMENTS

| 0210540 | 2/1987 | European Pat. Off. . |
| 0250374 | 12/1987 | European Pat. Off. . |
| 0305418 | 3/1989 | European Pat. Off. . |
| 0315414 | 5/1989 | European Pat. Off. . |

OTHER PUBLICATIONS

Remingtons Pharmaceutical Sciences., Mack Publishing Co. 1985.

*Primary Examiner*—Thurman K. Page
*Attorney, Agent, or Firm*—Sprung Horn Kramer & Woods

[57] ABSTRACT

Controlled release medicament pellets comprising
a) a core which contains as active ingredient a compound of the formula

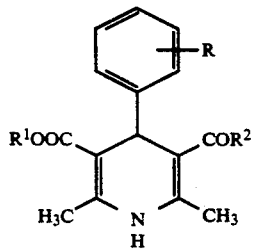

or a compound from the group of 3-(4-fluorophenyl-sulphonamido)-1,2,3,4-tetrahydro-9-carbazole propanoic acid or 2-[4-[4-(2-pyrimidinyl)-1-piperazinyl]-butyl]-1,2-benzisothiazol-3 (2H)-one 1,1-dioxide monohydrochloride, an intensive disintegrating agent, a wetting agent and a binder,
b) a double layer which controls release comprising
  (b1) an acrylic-based outer undigestible water-permeable lacquer layer, and
  (b2) an inner jacket layer comprising a hydrophobic additive and hydroxypropylcellulose of type M or H.

9 Claims, 2 Drawing Sheets

MEDICAMENTS HAVING CONTROLLED RELEASE OF THE ACTIVE COMPOUND

The invention relates to a new active compound release system in pellet form with which the release of active compound can be controlled with respect to time, can be established in pulsed form and can also be adjusted in its particular gradient. The pellets according to the invention consist of a core which contains the active compound and is surrounded by a polymer-containing jacket and an undigestible lacquer layer which is permeable to water.

The therapeutic benefit of a medicament is determined not only by the nature of the active compound used but to a high degree by the specific galenical presentation form. In the case of many medicaments, optimization of the formulation form increases the action efficacy, reduces the undesirable side effects, increases the treatment reliability and at the same time improves patient compliance. By means of special galenical formulations, the active compound reaches the absorption organ at the correct point in time and in the optimum dosage (compare K. Heimann, Therapeutic Systems, Rate-controlled Drug Delivery; Concept and Development; New York (1984) Thieme Stratton).

There are numerous attempts at developing systems, even for sparingly soluble active compounds, which should guarantee controlled release, with respect to time and location, of the active compound in optimum concentrations. Thus, for example, attempts have been made to achieve continuous or discontinuous release, controlled with respect to time, of active compounds via osmotic mechanisms by forcing the active compound out of a given opening (compare DE-A1 3,715,227).

The possibility of continuous release, controlled with respect to time, has also been attempted with erosion systems or with lacquered systems, the lacquer layer being a partly membrane having a retarding action (compare WO 88/00046). However, a disadvantage of such continuously releasing systems is the fact that the release of active compound often decreases in time, and in the case of non-eroding matrix systems and lacquered systems the disadvantage is that the active compound often is not released quantitatively. Further disadvantages which may be mentioned for these systems are the fact that, for example, the osmotic systems are very complicated and expensive to prepare, and often the known disadvantages of individual dose medicament forms occur, such as, for example, dose dumping and wide variability in the passage time in the body, according to the individual and diet. Moreover, multi-pulsed bursts of release cannot be realized in practice with these systems.

To avoid the disadvantage of the release of active compound decreasing with time, attempts have also been made to prepare multi-layered tablets having a different concentration of active substance in the various layers (DE-OS) (German Published Specification) 1,767,765), or to increase the concentration of the active compound from the shell to the core with an increasing concentration gradient (compare German Patent Specification 2,651,176). Such formulation forms can be prepared only with great technical effort, do not allow bursts of release of any desired frequency and in tablet form are subject to a high degree to the different passage times and dietary habits of the patient.

To avoid some of these disadvantages, tablets or capsules with controlled release of the active compound which contain a relatively large number of small dosage units in the form of cores, beads, granules or pellets have also been proposed (see DE-OS (German Published Specification) 1,617,724 and U.S. Pat. No. 3,247,066). The beads or pellets described therein are said to release the medicament over a period of up to 12 hours. As a result of the dimensions and large number of small beads, the release functions largely independently of the various physiological conditions of individual patients. The cores, containing the active compound, of these beads or pellets are surrounded by an undigestible film which is permeable to water and readily tears. In addition to the active compound, the core contains a colloid which is swellable in water. On contact with the water-containing body fluid, the core starts to absorb water and to swell, which in the end, after a certain period of time, leads to bursting of the film coating and to increased release or absorption of the active compound released. The start of the main absorption is some time after the time of intake and can largely be controlled via the nature and thickness of the film coating and the nature and amount of the swelling substances. Gelatine is mentioned as the preferred swelling colloid and ethylcellulose is mentioned as the preferred material for the lacquer shell. The aim of this application is controlled release of the active compound regardless of the pH of the various body fluids, for example acid gastric juice and alkaline intestinal fluid.

One disadvantage of this system is that active compound contents can already be released by diffusion before the lacquer layer tears. Furthermore, although delay times can be achieved by this system, the gradient which can be achieved in the subsequent release of active compound after bursting of the shell is not optimum. A steep release of active compound is desirable in particular for active compounds having a "first pass effect" which can be saturated, in order to achieve a good bioavailability with little stress on the organism from the active compound. Another disadvantage is that in these core-lacquer pellets, the active compound is already wetted with the aqueous release medium very early on. This can means that undesirable reactions of the body fluid with the active compound already take place hours before the lag time is reached, such as, for example, recrystallization and therefore a change in the solution and absorption properties or chemical changes to the active compound.

One variant of this "bursting" medicament form is also described in European Patent A-210,540. The principle, called in that specification a "time-controlled explosion system", for controlled release of the active compound is distinguished by the fact that a hydrophilic layer containing powerful swelling agents or disintegrating agents lies directly underneath a water-permeable lacquer layer or membrane. These layers are either free of active compound (compare FIGS. 1 and 2) or already contain active compound (compare FIGS. 3 and 4). As a result of the direct contact of the disintegrating agents or swelling layer with the outer membrane, the explosion pressure starts to build up in this system immediately after water has diffused through the outer membrane. As a result of this build-up, it is difficult to guarantee lag times of several hours. The release data of Table 1 show different lag times for the various layers of the ethylcellulose membrane, and these are only less than 4 hours even with a very thick ethylcellulose layer which makes up about 30% of the weight (sample C). The publication by Satoshi Ueda et al. in Proceed Intern. Symp. Control. Rel. Bioact. Mater., 15 (1988) Controlled Release Society, Inc., No. 254, pages 450–451 also demonstrates this. The results presented there, in particular FIG. 3, show that the maximum lag time which can be achieved in this system is less than 5 hours, it already being impossible to achieve the desired gradient in the release curve after this time.

In contrast, the active compound release system according to the invention exhibits a number of advantages. Any desired release profiles, even over a period of more than 12 hours, can be realized by combination of the pellets according to the invention, for example by using different pellet groups. The long delay times, which have not been possible to date, after which very steep releases or even less steep releases can then be programmed as desired are of particular advantage. The increased breakdown of the active compound in a first pass effect which can be saturated is overcome by this pulsed, controllable active compound release at any desired interval of time. This allows a reduction in the dose because of the reduced metabolization and avoids unnecessary stress to the metabolizing organs. The active compound release can be adapted to suit the daytime requirement or the biological rhythm by suitable combination of pellet groups with different release properties. According to this system, the active compounds can likewise be provided in certain absorption sections (absorption windows) in different regions of the gastrointestinal tract. Premature enzymatic, bacterial or chemical breakdown of the active compound is in this way excluded. Unnecessary irritation in the absorption organs is avoided. At the same time, the risk of intake at the wrong time by the patient is reduced. The independence of the desired delay time from the various pH values and eating habits increases the medicament reliability and the efficacy of the treatment.

The present invention relates to new medicaments having controlled release of the active compound and containing at least one pellet group, characterized in that the pellets are built up from a) a core which contains as an active substance a compound of the general formula

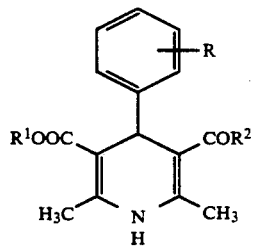

in which
R represents nitro or the group

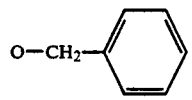

in the ortho- or meta-position, $R^1$ represents alkyl having 1–4 C atoms, which is optionally interrupted by an oxygen in the chain, and $R^2$ represents alkoxy having 1–4 C atoms, or represents the radical

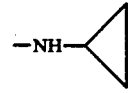

or a compound from the group of 3-(4-fluorophenylsulphonamido)-1,2,3,4-tetrahydro-9-carbazole propanoic acid or 2-[4-[4-(2-pyrimidinyl)-1-piperazinyl]butyl]-1,2-benzisothiazol-3(2H)-one 1,1-dioxide e.g. as monohydrochloride salt, an intensive disintegrating agent from the group comprising crosslinked sodium carboxymethylcellulose or sodium starch glycolate (NF XVI), sodium laurylsulphate as a wetting agent and Polyvinylpyrrolidon e.g. PVP-25 as a binder, and b) a double layer which controls the release, consisting of b1) an outer undigestible water-permeable lacquer layer which essentially consists of acrylic resins based on poly(meth)acrylic acid esters having a neutral character (NE type) or having a low content of quaternary ammonium groups (R type), the NE type consisting of copoly(meth)acrylic acid esters having the structural element

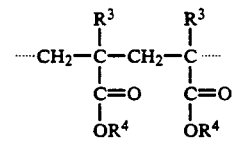

wherein
$R^3$ represents H or $CH_3$ and
$R^4$ represents $CH_3$ or $C_2H_5$,
and having an average molecular weight of about 800,000, and
the R type differing from this in that $R^4$, in a molar ratio of 1:20 to 1:40, represents the group

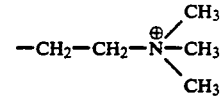

and it has an average molecular weight of about 150,000, or
consists essentially of ethylcellulose, and wherein such outer layer (b1) may contain additionally auxiliary agents such as anti adhesives as magnesium stearate or calcium stearate and conventional plasticizers such as polyethylene glycol 20,000, dialkyl (1–4 C atoms) diphthalate, glycerol triacetate or citric acid esters, such as triethyl citrate, and b2) an inner jacket which controls the migration of the water in the direction of the core and consists of 10 to 40% of hydroxypropylcellulose of type M or H (HPC-M or HPC-H) and consists to the extend of 60% to 90% of a hydrophobic additive, such as calcium stearate or hydrogenated castor oil.

Pellets having a particle diameter of 0.8 to 3.5 mm, preferably of 1.0 to 3 mm, in particular 1.5 to 2.5 mm, and weighing 0.5–20 mg, in particular 2–10 mg per pellet, are of particular interest. The weight content of the core containing the active compound is 20–50%, in particular 25–40% of the total weight of the pellet, and the core preferably has a diameter of 0.5–1.5 mm. The content of dihydropyridine active compounds in the core is preferably 40–90%, in particular 60–85% of the core weight.

The outer lacquer layer is preferably up to 0.3 mm, in particular up to 0.2 mm thick. The weight of the lacquer layer is up to 50%, in particular up to 35%, based on the total weight of the pellet.

The migration-controlling jacket layer has a thickness of about 0.1 to 0.5 mm, in particular 0.2 to 0.4 mm. The weight of this jacket layer is about 25–65%, in particular 30–55% of the pellet weight.

The content of hydroxypropylcellulose in the jacket is about 10 to 40%, in particular 15 to 30% of the total jacket weight, and the content of the lipophilic constituent of the jacket is, in particular, 70 to 85% of the weight of the jacket layer.

The core contains the dihydropyridine active compounds in a weight ratio of 40 to 90%, in particular 50 to 85%, based on the core weight. The content of intensive disintegrating agent is about 3 to 30%, in particular 5 to 20% of the core weight. The wetting agent content (sodium laurylsulphate) of the core weight is 0.5 to 5%, in particular 1 to 3%, and the binder content (PVP-25) is about 3 to 25%, in particular 5 to 20% of the core weight.

The formulation according to the invention is particularly suitable for the active compounds nifedipine, nimodipine, nisoldipine and methyl-4-(2-benzyloxyphenyl)-5-cyclopropyl -carbamoyl-1,4-dihydro-2,6-dimethyl-pyridine-3-carboxylate, both in racemic form and as the enantiomers and 3-(4-fluorophenylsulphonamido)-1,2,3,4-tetrahydro-9-carbazole-propanoic acid and 2-[4-[4-(2-pyrimidinyl)-1-piperazinyl]butyl]-1,2-benzisothiazol-3-(2H)-1,1-dioxide monohydrochloride.

The core preferably contains crosslinked sodium carboxymethylcellulose (croscarmellose sodium USP XXI N.F. 16 type A) as the intensive disintegrating agent, sodium laurylsulphate as the wetting agent and polyvinylpyrrolidone 25 (PVP 25) as the binder.

The jacket preferably contains hydroxypropylcellulose in the form of HPC-M or HPC-H, and calcium stearate as the lipophilic additive.

The lacquer preferably contains poly(meth)acrylic acid esters of the types RS, RL and NE30D, in particular the polymers known by the tradenames Eudragit RS ®, Eudragit RL ® and Eudragit NE30D ®, which are marketed by the company Roehm Tech. Inc., USA.

By the combination according to the invention of a water-permeable but insoluble lacquer layer with a jacket layer which contains no active compound and controls the migration of the water to the core as a result of a certain mixture of hydrophobic and hydrophilic constituents, without leading to bursting of the lacquer shell, with the active compound-containing core which contains the active compound and at the same time intensive disintegrating agents, the release of the active compound from the particular pellets can be delayed for a period of more than 12 hours. Pulsed release which, with a single daily intake, can be adapted to suit the different active compound requirement of the daily rhythm of the patient can be achieved by combination of different pellet groups. This is of importance above all for long-term therapy, for example of high blood pressure. Thus, for example, the phase of low blood pressure during the night can be coordinated with a corresponding lag phase, so that the delayed release coincides with the increase in blood pressure in the early hours of the morning.

The gradient of the release can be controlled via the content of the disintegrating agent portion in the core. Very narrow release intervals can be achieved even after delay times of more than 6 hours.

The standardized release interval (SRI) may be defined as follows: $SRI = (t80 - t20)/t50$, $t80$ being the time at which 80% of the active compound is released, and analogously $t20$ and $t50$ being the time at which 20 and 50% respectively of the active compound is released. An SRI of less than 0.25, in particular 0.20, can be achieved by the pellets according to the invention even after a delay time of more than 6 hours.

Another characteristics of the pellets according to the invention is that less than 5% of the active compound is released in up to 90% of the lag time. This allows very precise adjustment of the retarded or pulsing bursts of release.

Slower releases, that is to say higher SRI values, can of course also be achieved by means of the pellets according to the invention, for example by reducing the disintegrating agent content in the core. Uniform (non-pulsed) releases can likewise be realized, for example by using a higher number of pellets, the lag times of which are distributed uniformly over the entire release period.

Surprisingly, very long delay times with only thin layers of the placebo content of the small pellets can be achieved by the synergistic interaction of the lacquer layer and jacket layer. In the formulations known to date, the lag time or the delay period was controlled only via 1 or 2 parameters, for example only by erosion or, as in European Patent A-210,540, on the one hand by the water-permeable lacquer layer and on the other hand by the nature and amount of the disintegrating agent in the adjacent jacket region. In the system according to the invention, the jacket layer free from active compound provides a further control parameter for the delay time. The lacquer and jacket layer allow effective control of the rate of migration of the water to the core. They ensure uniform penetration of the water front and therefore very precise control of the lag times with steep releases. The expert is therefore for the first time in a position to employ the known advantageous of pellets having a particle diameter of less than 3 mm for sustained release formulations or for long-acting formulations, adjusted to suit the daily rhythm, with pulsed release.

Customary galenical measures can also be used without problems for the pellets according to the invention. Thus, for example, the lacquer and/or jacket layer can be stained with customary medicament dyestuffs for the purpose of light stabilization or for better distinguishability, and salts which influence the osmosis or the pH or flavor improvers can be added.

The pellets according to the invention are prepared by customary methods. The core can be prepared in a continuous or discontinuous procedure by, for example, rolling granulation, mixing granulation, fluidized bed granulation or fluidized bed spraying granulation or by tabletting. Mixing granulation and rolling granulation methods, for example plate, drum and rotor granulation, are particularly preferred. The constituents of the core (active compound, disintegrating agent and auxiliaries) preferably have particle sizes of less than 100 μm in order to achieve a high spherically or surface quality.

The core is prepared, for example, by mixing the active compound, the intensive disintegrating agent, the wetting agent and the binder in a mixer, adding water and/or organic solvents, such as lower aliphatic alcohols or acetone, as the granulating liquid, granulating for 0.5-3 hours and then drying at 30°-120° C., preferably 40°-100° C. The resulting granules are then sieved.

The jacket layer is likewise applied to the cores by customary methods, for example by spraying on from a solution, melt or suspension. The process can be carried out in a mechanical mixer, in a fluidized bed, on a granulating plate, in a granulating drum or in a rotor granulator. The jacket material can also be applied in powder form with addition of granulating liquid, for example in a discontinuous or continuous manner in the apparatuses customary for rolling granulation.

The hydrogel-forming agent hydroxypropylcellulose (HPC-M or HPC-H) is preferably employed with a particle size of less than 100 μm, in particular less than 65 μm, in the preparation of the jacket layer.

The lacquer is applied in the customary manner, for example by spraying on from an organic solution or from an aqueous suspension in lacquering kettles, rotating drums or plates or in customary coaters. The lacquer is preferably applied from an aqueous dispersion at elevated temperatures at which film formation occurs, preferably at 30°-100° C., in particular at 40°-80° C.

In the case of application of the lacquer from a solution, organic solvents from the group comprising lower aliphatic alcohols, such as ethanol, methanol and isopropanol, volatile ketones, such as, for example, acetone, and halogenated hydrocarbons, such as, for example, methylene chloride or chloroform, are preferably employed.

Capsules are filled with the mixed or non-mixed pellet groups using the customary filling and sealing machines. In addition to filling the capsules with pellets, it is also possible to introduce the pellets into a compressed tablet. A preferred process for the preparation of the pellets according to the invention comprises a procedure in which a) the core is prepared by mixing the active compound, the disintegrating agent, the wetting agent and the binder, subsequently granulating the mixture for 0.5 to 3 hours with the addition of water and/or organic solvents, such as lower aliphatic alcohols or acetone, as the granulating liquid and then drying the mixture at 30° to 120° C. and sieving the resulting granules, and b) the jacket layer is applied by spraying from a solution, melt or suspension of the hydroxypropylcellulose and the hydrophobic additive in a fluidized bed, on a granulating plate, in a mechanical mixer or in a rotor granulator, or the jacket material is applied in powder form, with addition of granulating liquid, in a discontinuous or continuous manner in apparatuses customary for rolling granulation, and c) the lacquer constituents are either sprayed on as a solution in organic solvents, such as lower aliphatic alcohols, volatile ketones or halogenated hydrocarbons, or applied from an aqueous suspension in lacquering kettles, rotating drums or plates or in customary coaters at temperatures between 30° and 100° C. and are crosslinked by means of heat.

The release of the pellets according to the invention is determined in accordance with the USP paddle method. In each case capsules filled with pellets and containing 30 mg of active compound are employed. The test is carried out at 37° C. in 4,000 ml. of release medium at 100 revolutions per minute. The release medium is brought to pH 6.8 with a buffer (DAB-9; diluted 1:10) and additionally contains 0.25% of sodium laurylsulphate and 0.68% of sodium chloride.

The administration forms which can be prepared from the pellets according to the invention, such as capsules or compressed tablets, can be prepared by customary methods, combinations with other active compounds also being possible. If immediately acting initial doses are desired, the pellets according to the invention can also be combined with fast-releasing forms of the abovementioned dihydropyridines, for example with coprecipitates or with non-lacquered cores.

Figure 2:
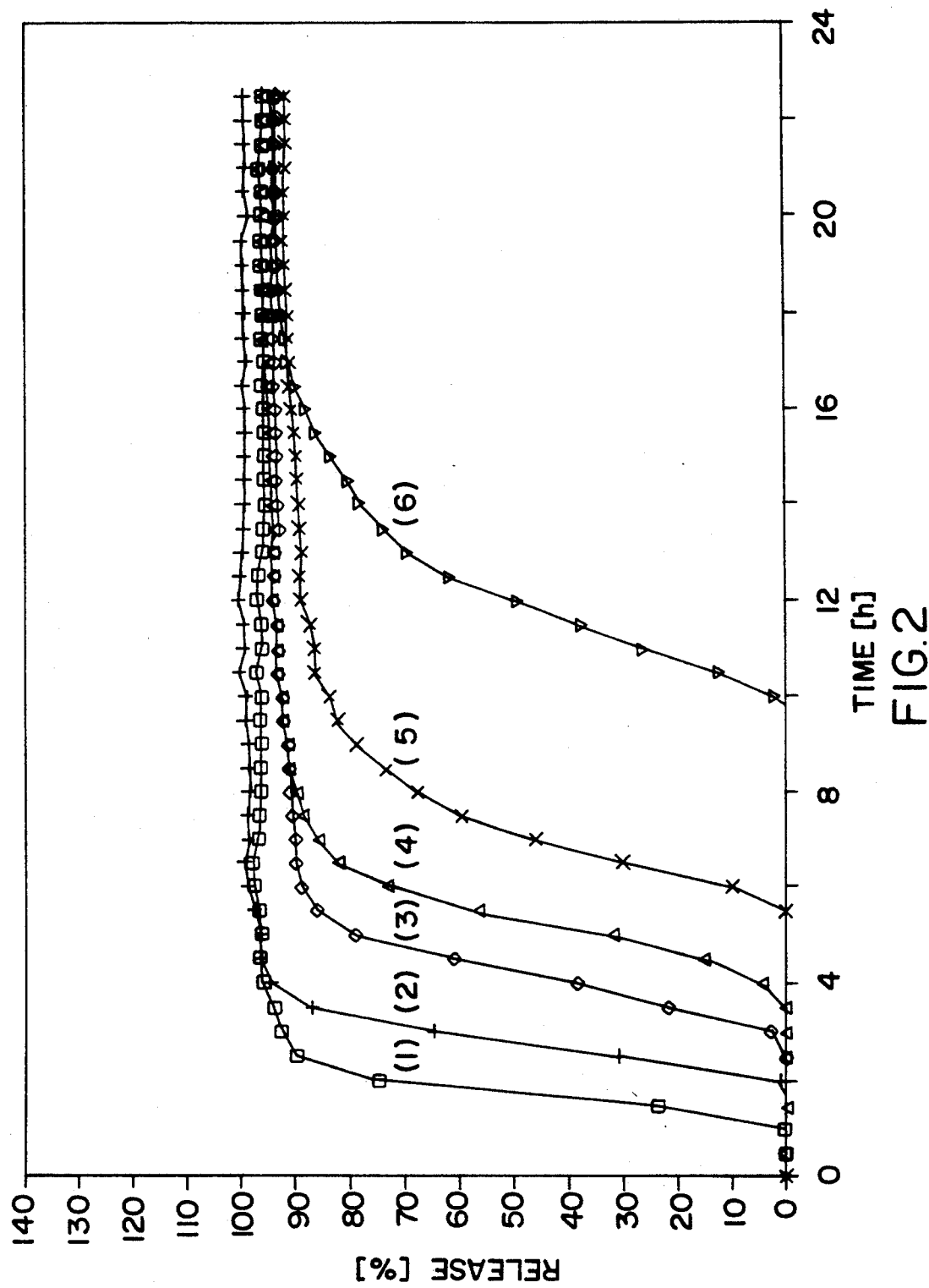

The invention is further described in the following examples which illustrate the core-jacket pellets (CJL pellets) according to the invention, in conjunction with the accompanying drawings wherein:

FIGS. 1 and 2 are plots showing the rate of release of active material.

EMBODIMENT EXAMPLES

Example 1

Preparation of the core 850 g of micronized nifedipine are mixed with 80 g of crosslinked sodium carboxymethylcellulose, 50 g of PVP-25 and 20 g of sodium laurylsulphate in an intensive mixer. 200 ml of distilled water are then added and granulation is carried out for 3 hours at room temperature with a decreasing speed of rotation (3,000→400 revolutions per minute). The resulting cores are dried at 80° C. and sieved (diameter 1.25-1.5 mm).

Application of the jacket 1,000 g of these cores are initially introduced into a rotor granulator and a mixture of 510 g of hydroxypropylcellulose M (corresponding to 30% of the jacket content) and 1,190 g of hydrogenated castor oil (corresponding to 70% of the jacket content) and water as the granulating liquid is added continuously and the cores ar coated with a jacket in a rotor granulator (250 revolutions per minute) at room temperature. (Dose rate of the powder 1,000 g/hour). The bed moisture content is regulated here at 25% absolute moisture by metering the granulating liquid. Lacquer application The jacketed cores (2,700 g) are sprayed at 60°-70° C. in a rotor coater with a 10% strength aqueous dispersion consisting of 50.6% of Eudragit RS, 44.9% of magnesium stearate and 4.5% of PEG 20,000, in each case based on the weight of the solid content. After 1.5 hours, pellet groups with a lacquer content of 30% are obtained. Pellets with a lacquer content of 80% are obtained after 4.0 hours.

The following delay times results, depending on the thickness of the lacquer layer:

| Amount of lacquer layer based on the core weight | Delay time |
| --- | --- |
| 0 % (no lacquer) | 1.5 hours |
| 30 % | 4.0 hours |

| Amount of lacquer layer based on the core weight | Delay time |
|---|---|
| 80 % | 8.5 hours |

Example 2

Core-jacket-lacquer pellets of the following recipe are prepared analogously to Example 1:

| | Parts by weight: |
|---|---|
| Core (1 part) | |
| Nifedipine | 73% |
| Crosslinked sodium carboxymethyl-cellulose | 15% |
| PVP 25 | 10% |
| Sodium laurylsulphate | 2% |
| Jacket (1.7 parts) | |
| Hydroxypropylcellulose M | 30% |
| Calcium stearate | 70% |
| Lacquer (0.1–1.09 parts) | |
| Eudragit RS | 50.6% |
| Magnesium stearate | 44.9% |
| PEG 20,000 | 4.5% |

| Curve | Amount of lacquer applied based on the core weight = 100% | Delay time |
|---|---|---|
| 1 | 0% (no lacquer) | 1.0 hour |
| 2 | 10% | 2.0 hours |
| 3 | 28% | 4.0 hours |
| 4 | 44% | 5.6 hours |
| 5 | 64% | 7.0 hours |
| 6 | 109% | 12 hours |

The release rates for the various lacquer amounts can be seen from FIG. 1.

Example 3

CJL pellets of the following recipe were prepared analogously to Example 1:

| | Parts by weight: |
|---|---|
| Core (1 part) | |
| Nisoldipine | 73% |
| Crosslinked sodium carboxymethyl-cellulose | 15% |
| PVP 25 | 10% |
| Sodium laurylsulphate | 2% |
| Jacket (1.7 parts) | |
| Hydroxypropylcellulose M | 30% |
| Calcium stearate | 70% |
| Lacquer (0.11–1.07 parts) | |
| Eudragit RS | 50.6% |
| Magnesium stearate | 44.9% |
| PEG 20,000 | 4.5% |

| Curve | Amount of lacquer applied based on the core weight = 100% | Delay time |
|---|---|---|
| 1 | 0% (no lacquer) | 1.0 hour |
| 2 | 11% | 2.0 hours |
| 3 | 29% | 3.0 hours |
| 4 | 43% | 4.0 hours |
| 5 | 63% | 5.5 hours |
| 6 | 107% | 10 hours |

The release rates for the various lacquer amounts can be seen from FIG. 2.

Example 4

CJL pellets of the following recipe were prepared analogously to Example 1:

| | Parts by weight: |
|---|---|
| Core (1 part) | |
| Nimodipine | 73% |
| Crosslinked sodium carboxymethyl-cellulose | 15% |
| PVP 25 | 10% |
| Sodium laurylsulphate | 2% |
| Jacket (1.3 parts) | |
| Hydroxypropylcellulose M | 30% |
| Calcium stearate | 70% |
| Lacquer (0.1–1.07 parts) | |
| Eudragit RS | 50.6% |
| Magnesium stearate | 44.9% |
| PEG 20,000 | 4.5% |

| Amount of lacquer applied based on the core weight = 100% | Delay time |
|---|---|
| 0% | 0.7 hour |
| 10% | 1.5 hours |
| 29% | 3.4 hours |
| 48% | 5.1 hours |
| 67% | 6.5 hours |
| 107% | 10.3 hours |

Example 5

CJL pellets of the following recipe were prepared analogously to Example 1:

| | Parts by weight |
|---|---|
| Core (1 part) | |
| Nisoldipine | 60% |
| Sodium starch glycolate | 23% |
| PVP 25 | 15% |
| Sodium laurylsulphate | 2% |
| Jacket (1.2 parts) | |
| Hydroxypropylcellulose H | 20% |
| Hydrogenated castor oil | 80% |
| Lacquer (0.1–1.2 parts) | |
| Eudragit NE30D | 55% |
| Magnesium stearate | 44% |
| Glycerol triacetate | 1% |

Example 6

CJL pellets of the following recipe were prepared analogously to Example 1:

| | Parts by weight |
|---|---|
| Core (1 part) | |
| 4-(2-benzyloxyphenyl)-1,4-dihydro-2.6-dimethylpyridine-(3-carboxylic acid methyl ester)-(5-carboxylic acid cyclopropylamide) | 70% |
| Sodium starch glycolate | 18% |
| PVP 25 | 10% |
| Sodium laurylsulphate | 2% |
| Jacket (1 part) | |
| Hydroxypropylcellulose H | 30% |
| Calcium stearate | 70% |
| Lacquer (0.1–1.2 parts) | |
| Eudragit NE30D | 50.6% |
| Magnesium stearate | 44.9% |
| PEG 20.000 | 4.5% |

It is understood that the specification and examples are illustrative but not limitative of the present invention and that other embodiments with the spirit and scope of the invention will suggest themselves to those skilled in the art.

We claim:

1. Pellets of a medicament having controlled release of the active compound and comprising
(a) a core which contains
(a1) an active compound of the formula

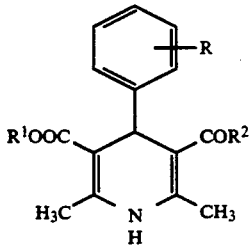

in which
R represents nitro or the group

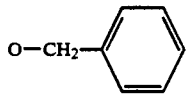

in the ortho- or meta-position,
$R^1$ represents alkyl having 1–4 C atoms, which is optionally interrupted by an oxygen in the chain, and
$R^2$ represents alkoxy having 1–4 C atoms, or represents the radical

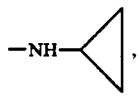

or a compound from the group consisting of 3-(4-fluorophenylsulphonamido)-1,2,3,4-tetrahydro-9-carbazole propanoic acid and 2-[4-(2-pyrimidinyl)-1-piperazinyl] butyl]-1,2-benzisothiazol-3(2H)-one, 1,1-dioxide, and
(a2) an intensive disintegrating agent from the group comprising crosslinked sodium carboxymethylcellulose or sodium starch glycolate, and
(a3) sodium laurylsulphate as a wetting agent, and
(a4) PVP as a binder, and
b) a double layer which controls the release, consisting of
b1) an outer undigestible water-permeable lacquer layer which essentially consists of an acrylic resin based on a poly(meth)acrylic acid ester having a neutral character or having a low content of quaternary ammonium groups, consisting of a copoly(meth)acrylic acid ester having the structural element

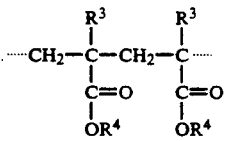

wherein
$R^3$ represents H or $CH_3$ and
$R^4$ represents $CH_3$ or $C_2H_5$,
and having an average molecular weight of about 800,000, and
the said ester having the low content of quaternary ammonium groups differing in that the $R^4$, in a molar ratio of 1:20 to 1:40, represents the group

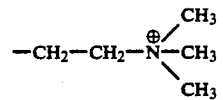

and it has an average molecular weight of about 150,000, or consists essentially of ethylcellulose, optionally contains antiadhesive agents, and
b2) an inner jacket which controls the migration of the water in the direction of the core and consists essentially of about 10 to 40% of hydroxypropylcellulose and about 60 to 90% of a hydrophobic additive selected from the group consisting of calcium stearate and hydrogenated castor oil.

2. Pellets according to claim 1, wherein the intensive disintegrating agent of the core is crosslinked sodium carboxymethylcellulose, the lacquer layer (b1) comprises a polymethacrylic acid, and the jacket (b2) contains calcium stearate as the hdyrophobic additive.

3. Pellets according to claim 1 having a particle diameter of 0.8 to 3.5 mm.

4. Pellets according to claim 1, wherein the content of active compound in the core is 40 to 90%, based on core weight.

5. Pellets according to claim 1, wherein the lacquer layer has a thickness of up to 0.3 mm and its weight is up to 50% of the total weight of the pellets.

6. Pellets according to claim 1, wherein the jacket layer has a thickness of about 0.1 to 0.5 mm.

7. Pellets according to claim 1, wherein the outer layer (b1) additionally contains at least one of (c) an anti adhesive selected from the group consisting of magnesium stearate and calcium stearate, and (d) a plasticizer selected from the group consisting of polyethylene glycol, a $C_{1-4}$-dialkyl phthalate, glycerol triacetate and a citric acid ester.

8. Pellets according to claim 1, wherein the active compound is selected from the group consisting of nifedipine, nimodipine, nisoldipine, methyl-4-(2-benzyloxyphenyl)-5-cyclopropyl-carbamoyl-1,4-dihydro-2,6-dimethyl-pyridine-2-carboxylate, 3-(4-fluorophenyl-sulphonamido)-1,2,3,4-tetrahydro-9-carbazole-propanoic acid and 2-[4-[4-(2-pyrimidinyl)-1-piperazinyl]butyl]-1,2-benzisothiazol-3-(2H)-one 1,1-dioxide monohydrochloride.

9. A process for the preparation of pellets according to claim 1, comprising
a) mixing the active compound, the disintegrating agent, the wetting agent and the binder, subsequently granulating the mixture in a rotor granulator for 0.5 to 3 hours with the addition of water and/or an organic solvent, as the granulating liquid, drying the mixture at 30° to 120° C. to form granules and sieving the granules, thereby to form the cores,
b) applying to the cores a jacket material in powder form along with addition of a granulating liquid, and
c)
(i) spraying onto the jacketed cores the lacquer constituents as a solution in an organic solvent, or
(ii) applying to the jacketed cores an aqueous suspension of the lacquering substituents at a temperature between 30° and 100° C., and crosslinking by means of heat.

* * * * *

UNITED STATES PATENT AND TRADEMARK OFFICE
CERTIFICATE OF CORRECTION

PATENT NO. : 5,204,121

DATED : April 20, 1993

INVENTOR(S) : Bucheler et al.

It is certified that error appears in the above-identified patent and that said Letters Patent is hereby corrected as shown below:

Title Page    FOREIGN PATENT DOCUMENTS: Delete " 0305418 " and substitute -- 0305918 --

Col. 11, line 39    Delete " 2-[4-(2- " and substitute -- 2-[4-[4-(2- --

Col. 12, line 45    Delete " 2-carboxylate " and substitute -- 3-carboxylate --

Signed and Sealed this

Sixteenth Day of August, 1994

Attest:

BRUCE LEHMAN

Attesting Officer    Commissioner of Patents and Trademarks